US008975295B2

(12) United States Patent
Waugh

(10) Patent No.: US 8,975,295 B2
(45) Date of Patent: Mar. 10, 2015

(54) MODULATION OF ZINC LEVELS TO IMPROVE TISSUE PROPERTIES

(75) Inventor: Jacob M. Waugh, Palo Alto, CA (US)

(73) Assignee: Precision Dermatology, Inc., Cumberland, RI (US)

(*) Notice: Subject to any disclaimer, the term of this patent is extended or adjusted under 35 U.S.C. 154(b) by 0 days.

(21) Appl. No.: 10/692,191

(22) Filed: Oct. 22, 2003

(65) Prior Publication Data

US 2004/0157921 A1    Aug. 12, 2004

Related U.S. Application Data

(60) Provisional application No. 60/421,278, filed on Oct. 25, 2002, provisional application No. 60/421,336, filed on Oct. 25, 2002.

(51) Int. Cl.

| | |
|---|---|
| A61K 31/315 | (2006.01) |
| A61K 33/32 | (2006.01) |
| A61K 8/02 | (2006.01) |
| A61L 29/10 | (2006.01) |
| A61K 8/27 | (2006.01) |
| A61K 31/555 | (2006.01) |
| A61K 33/30 | (2006.01) |
| A61L 29/14 | (2006.01) |
| A61L 31/08 | (2006.01) |
| A61L 31/14 | (2006.01) |
| A61Q 11/00 | (2006.01) |
| A61Q 19/00 | (2006.01) |
| A61Q 19/06 | (2006.01) |
| A61Q 19/08 | (2006.01) |

(52) U.S. Cl.
CPC .............. *A61L 29/106* (2013.01); *A61K 8/27* (2013.01); *A61K 31/315* (2013.01); *A61K 31/555* (2013.01); *A61K 33/30* (2013.01); *A61L 29/14* (2013.01); *A61L 31/088* (2013.01); *A61L 31/14* (2013.01); *A61Q 11/00* (2013.01); *A61Q 19/00* (2013.01); *A61Q 19/06* (2013.01); *A61Q 19/08* (2013.01)
USPC ........................... 514/494; 424/642; 424/401

(58) Field of Classification Search
CPC ....... A61K 33/30; A61K 31/315; A61K 8/27; A61Q 19/08
See application file for complete search history.

(56) References Cited

U.S. PATENT DOCUMENTS

| | | | |
|---|---|---|---|
| 4,261,982 A | 4/1981 | Lueddres | |
| 4,704,280 A | 11/1987 | Bates | |
| 4,895,727 A | 1/1990 | Allen | |
| 4,938,969 A | 7/1990 | Schinitsky et al. | |
| 5,296,500 A | 3/1994 | Hillebrand | |
| 5,401,730 A | 3/1995 | Sauvage et al. | |
| 5,554,375 A | 9/1996 | Pickart | |
| 5,554,647 A | 9/1996 | Perricone | |
| 5,667,791 A | 9/1997 | Hersh et al. | |
| 5,674,912 A | 10/1997 | Martin | |
| 5,792,449 A | 8/1998 | Bryce-Smith | |
| 5,866,142 A * | 2/1999 | Riordan | |
| 5,883,085 A | 3/1999 | Blank et al. | |
| 5,962,441 A | 10/1999 | Blank | |
| 5,962,517 A | 10/1999 | Murad | |
| 5,972,999 A | 10/1999 | Murad | |
| 6,071,543 A | 6/2000 | Thornfeldt | |
| 6,086,863 A | 7/2000 | Ritter et al. | |
| 6,113,636 A * | 9/2000 | Ogle | |
| 6,177,105 B1* | 1/2001 | Grekin | 424/520 |
| 6,190,407 B1 | 2/2001 | Ogle et al. | |
| 6,193,975 B1 | 2/2001 | Bonte et al. | |
| 6,197,330 B1 | 3/2001 | Rees et al. | |
| 6,197,813 B1 | 3/2001 | Hegenauer | |
| 6,217,914 B1 | 4/2001 | Meisner | |
| 6,238,678 B1 | 5/2001 | Oblong et al. | |
| 6,242,491 B1 | 6/2001 | Kaddurah-Daouk | |
| 6,248,370 B1 | 6/2001 | Harris | |
| 6,267,782 B1 | 7/2001 | Ogle et al. | |
| 6,284,802 B1 | 9/2001 | Bissett et al. | |

(Continued)

FOREIGN PATENT DOCUMENTS

| | | |
|---|---|---|
| EP | 1371640 | 12/2003 |
| JP | H04-076518 | 3/1992 |

(Continued)

OTHER PUBLICATIONS

Uitto J. "Connective Tissue Biochemistry of the Aging Dermis. Age-Related Alterations in Collagen and Elastin". Dermatol. Clin. Jul. 1986; 4(3):433-436, Abstract Only.*

(Continued)

*Primary Examiner* — Leslie A. Royds Draper
(74) *Attorney, Agent, or Firm* — Brian B. Shaw, Esq.; John E. Thomas, Esq.; Harter Secrest & Emery LLP

(57) ABSTRACT

Methods of altering properties of tissues, by providing an effective modifying amount of zinc, which may be in the form of zinc ions. This is accomplished through the use of topical compositions containing one or more zinc-containing components such as salts and/or other zinc compounds or complexes, particularly zinc acetate.

Altering properties of tissues includes increasing or decreasing fatty tissue, increasing or decreasing epidermal thickness, increasing elastin content, and preventing or treating gum regression or atrophy.

Also disclosed is the provision of a contact lens coated with a zinc-containing material, to improve vision by increasing elastin content of the lens of the eye through release of zinc ions.

11 Claims, 16 Drawing Sheets

(56) References Cited

U.S. PATENT DOCUMENTS

| | | | |
|---|---|---|---|
| 6,296,861 | B1 | 10/2001 | Perricone |
| 6,299,898 | B2 | 10/2001 | Rees et al. |
| 6,322,588 | B1 | 11/2001 | Ogle et al. |
| 6,558,710 | B1 | 5/2003 | Godfrey |
| 6,573,299 | B1 * | 6/2003 | Petrus |
| 2002/0197289 | A1 | 12/2002 | Chevalier et al. |
| 2003/0068297 | A1 | 4/2003 | Jain |
| 2003/0077332 | A1 | 4/2003 | Godfrey |

FOREIGN PATENT DOCUMENTS

| | | |
|---|---|---|
| JP | H09-230104 | 9/1997 |
| JP | 2002-293731 | 10/2002 |
| WO | 98/17269 | 4/1998 |
| WO | WO-99/62481 | 12/1999 |
| WO | 00/01733 | 1/2000 |
| WO | 00/51559 | 9/2000 |
| WO | 01/13865 | 3/2001 |

OTHER PUBLICATIONS

STN Registry File No. 546-46-3. "Zinc Citrate". STN Registry File. Retrieved from STN Feb. 29, 2008. One page.*

WrinkleReducer 101. "Preventing and Treating Skin Wrinkles". [Retrieved Aug. 10, 2010]. Retrieved from the Internet: <URL: http://www.wrinklereducer101.com/skin-wrinkles.php>.*

STN Registry File No. 3486-35-9. "Zinc Carbonate". STN Registry File. Retrieved from STN Feb. 21, 2014. One page.*

STN Registry File No. 557-34-6. "Zinc Acetate". STN Registry File. Retrieved from STN Feb. 24, 2014. One page.*

Singapore Written Opinion, (2005).

Tang et al., "Zinc Has an Insulin-Like Effect on Glucose Transport Mediated by Phosphoinositol-3-Kinase and Akt in 3T3-L1 Fibroblasts and Adipocytes," *J. Nutr* 131: 1414-1420 (2001).

Wu et al., "Activation of the EGF receptor signaling pathway in human airway epithilial cells exposed to metals," *Am J. Physiol* 277: L924-L931 (1999).

Ma et al., "Stimulatory effect of zinc on insulin-like growth factor-I and transforming growth factor-β1 production with bone growth of newborn rats," *Int J Mol Med* 8(6): 623-8 (2001).

Hansson et al., "Extracellular Zinc Ions Induces Mitogen-Activated Protein Kinase Activity and Protein Tyrosine Phosphorylation in Bombesin-Sensitive Swiss 3T3 Fibroblasts," *Arch Biochem and Biophys* 328 (2): 233-238 (Apr. 15, 1996).

Wang et al., "Expression and Characterization of Wild Type, Truncated, and Mutant Forms of the Intracellular Region of the Receptor-like Protein Tyrosine Phosphatase HPTPβ," *J Biol chem* 267(23):16696-16702 (Aug. 15, 1992).

Wells, "Molecules in Focus, EGF Receptor," *Int J Biochem Cell Biol* 31(6): 637-643 (1999).

Coulston et al., "Insulin-like Effect of Zinc on Adiopocytes," *Diabetes* 29(8): 665-667 (Aug. 1980).

Shisheva et al., "Insulinlike effects of zinc ion in vitro and in vivo: preferential effects on desensitized adiopocytes and induction of normoglycemia in streptozociin-induced rats," *Diabetes* 41(8): 982-988 (Aug. 1992).

May et al., "The Mechanism of the Insulin-like Effects of Ionic Zinc," *J Biol Chem* 257(8): 4362-4368 (Apr. 25, 1982).

Kiss et al., "Bombesin and zinc enhance the synergistic mitogenic effects of insulin and phosphocholine by a MAP kinase-dependent mechanism in Swiss 3T3 cells," *FEBS Lett* 415(1): 71-74 (1997).

Chausmer et al., "Zinc, Insulin and Diabetes," *J Am Coll Nutr* 17: 109-115 (1998).

Gomot et al., "Effect of Acute Zinc Deficiency on Insulin Receptor Binding in Rat Adipocytes," *Biol Trace Elem Res* 32: 331-335 (1992).

Herington, "Effect of Zinc on Insulin Binding to Rat Adipocytes and Hepatic Membranes and to Human Placental Membranes and IM-9 Lymphocytes," *Horm Metab Res* 17: 328-332 (1985).

Kremerskothen et al., Determination of phosphotyrosine phosphatase (PTPase) activity in normal and transformed cells *Mol Cell Biochem* 125: 1-9 (1993).

Li et al., "Antilipolytic Actions of Vanadate and Insulin in Rat Adipocytes Mediated by Distinctly Different Mechanisms," *Endocrinology* 138: 2274-2279 (1997).

Samet et al., "Tyrosine Phosphatases as Targets in Metal-Induced Signaling in Human Airway Epithelial Cells," *Am J Respir Cell Mol Biol* 21: 357-364 (1999).

Braiman et al., "Protein Kinase Cδ Mediates Insulin-Induced Glucose Transport in Primary Cultures of Rat Skeletal Muscle," *Mol Endocrinol* 13: 2002-2012 (1999).

Kanoh et al., "Thiazolidinedione Treatment Enhances Insulin Effects on Protein Kinase C-ζ/λ Activation and Glucose Transport in Adipocytes of Nondiabetic and Goto-Kakizaki Type II Diabetic Rats," *J Biol Chem* 275: 16690-16696 (Jun. 2, 2000).

Standaert et al., "Insulin Activates Protein Kinases C-ζ and C-λ by an Autophosphorylation-dependent Mechanism and Stimulates Their Translocation to GLUT4 Vesicles and Other Membrane Fractions in Rat Adipocytes," *J Biol Chem* 274: 25308-25316 (Sep. 3, 1999).

Csermely et al., "Zinc Can Increase the Activity of Protein Kinase C and Contributes to Its Binding to Plasma Membranes in T Lymphocytes," *J Biol Chem* 263:6487-6490 (May 15, 1988).

Forbes et al., "Zinc Induces Specific Association of PKC with Membrane Cytoskeleton," *Biochem Int* 22: 741-748 (Nov. 1990).

Forbes et al., "Interaction between protein kinase C and regulatory ligand is enhanced by a chelatable pool of cellular zinc," *Biochem Biophys Acta* 1053: 113-117 (1990).

Quest et al., "The Regulatory Domain of Protein Kinase C Coordinates Four Atoms of Zinc," *J Biol Chem* 267:10193-10197 (May 15, 1992).

Lynch et al., "Zinc stimulates the activity of the insulin- and nutrient-regulated protein kinase mTOR," *Am J Physiol Endocrinol Metab* 281(1): E25-E34 (2001).

Patti et al., "Bidirectional Modulation of Insulin Action by Amino Acids" *J Clin Invest* 101(7): 1519-1529 (Apr. 1998).

Martin et al., "Regulation of Ribosomal S6 Kinase 2 by Effectors of the Phosphoinositide 3-Kinase Pathway," *J Biol Chem* 276(11): 7884-7791 (Mar. 16, 2001).

Blobe et al., "Role of Transforming Growth Factor β in Human Disease," *N Engl J Med* 342(18): 1350-1358 (May 4, 2000).

Taipale et al., "Release of Transforming Growth Factor-β1 from the Pericellular Matrix of Cultured Fibroblasts and Fibrosarcoma Cells by Plasmin and Thrombin," *J Biol Chem* 267: 25378-25384 (Dec. 15, 1992).

Streuli et al., "Extracellular Matrix Regulates Expression of the TGF-β1 Gene," *J Cell Biol* 120: 253-260 (Jan. 1993).

Massague J., "How Cells Read TGF-β Signals," *Nat Rev Mol Cell Biol* 1(3): 169-178 (Dec. 2000).

Zhang et al., "Synergistic Cooperation between Sp1 and Smad3/Smad4 Mediates Transforming Growth Factor β1 Stimulation of α2(I)-Collagen (COL1A2) Transcription," *J Biol Chem* 275(50): 39237-39245 (Dec. 15, 2000).

Wotton et al, "A Smad Transcriptional Corepressor," *Cell* 97(1): 29-39 (Apr. 2, 1999).

Lo et al., "Epidermal growth factor signaling via Ras controls the Smad transcriptional co-repressor TGIF," *EMBO J* 20(1-2): 128-136 (2001).

Chvapil et al., "Inhibitory Effect of Zinc Ions on Platelet Aggregation and Serotonin Release Reaction," *Life Sciences* (16): 561-572 (1975).

Parks, "Posttranscriptional Regulation of Lung Elastin Production," *Am J Respir Cell Mol Biol* 17: 1-2 (1997).

Zhang et al., "An Open Reading Frame Element Mediates Posttranscriptional Regulation of Tropoelastin and Responsiveness to Transforming Growth Factor β1," *Mol Cell Biol* 9(11): 7314-7326 (1999).

Conn et al., "Insulin-like Growth Factor-I Regulates Transcription of the Elastin Gene through a Putative Retinoblastoma Control Element," *J Biol Chem* 271(46): 28853-28860 (Nov. 15, 1996).

Kahari et al., "Transforming Growth Factor-β Up-regulates Elastin Gene Expression in Human Skin Fibroblasts, Evidence for Post transcriptional Modulation," *Lab Invest* 66(5): 580-588 (May 1992).

(56) References Cited

OTHER PUBLICATIONS

Hinek et al., "67-kD Elastin-binding Protein Is a Protective 'Companion' of Extracellular Isoluble Elastin and Intracellular Tropoelastin," *J Cell Biol* 126(2): 563-574 (Jul. 1994).

Robert, "Interaction Between Cells and Elastin and the Elastin-receptor," *Connect Tissue Res* 40 (2): 75-82 (1999).

Nakamura et al., "The Epidermal Growth Factor Receptor (EGFR): Role in Corneal Wound Healing and Homeostasis", *Exp. Eye Res.*, 2001, 72:511-517.

Kryukova et al., "Effect of Local Application of Carbostimulin on the Enzyme Activity and Energy Metabolism in Alveolar Process Tissue of the Rat Jaw," Database Chemical Abstracts, XP002447281, Database Accession No. 100:96678, Aug. 15, 2007.

Tsuchiya et al., "Rabbit Eye Irritation caused by wearing Toxic Contact Lenses and Their Cytotoxicities: In vivo/in vitro Correlation Study Using Standard Reference Materials," Database Chemical Abstracts, XP002447282, Database Accession No. 119:188527; Aug. 15, 2007.

Supplemental European Search Report dated Aug. 30, 2007.

"Salicyclic Acid" retrieved on Apr. 15, 2009 from <<http://www.jtbaker.com/msds/englishhtml/s506.htm>>, May 4, 2007.

Maureen Martino, "Press Release: Paladin Labs Acquires Zincofax from Johnson & Johnson," retrieved on Apr. 12, 2009 from <<http://www.fiercebiotech.com/node/7035>>, May 30, 2007.

"Zincofax®" retrieved on Apr. 8, 2009 from <http://rxmed.com>>.

Ellen Byron, "Awards Promote Beauty Contest," retrieved on Apr. 9, 2009 from <<http:www.online.wsj.com/article/SB120459926954309547.html?mod=mm_hs_advertising>>, Mar. 4, 2008.

"Best of Beauty" issue of Allure Magazine, Oct. 2008, pp. 272-273, 288.

Joan C. Olson et al., "Efficient Production and Processing of Elastase and LasA by *Pseudomonas aeruginosa* Require Zinc and Calcium Ions," Journal of Bacteriology, Jun. 1992, pp. 4140-4147.

English translation of the Notification of Reasons for Refusal dated Apr. 22, 2010 in corresponding Japanese Patent Appln. No. 2004-548429.

\* cited by examiner

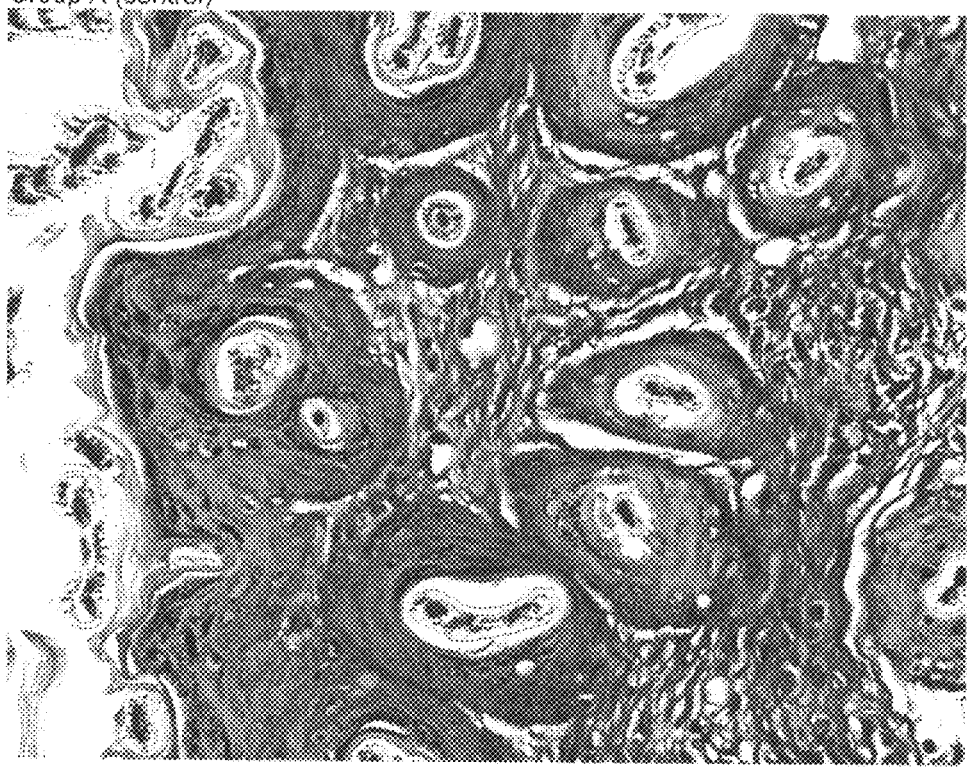

Group B

Group C

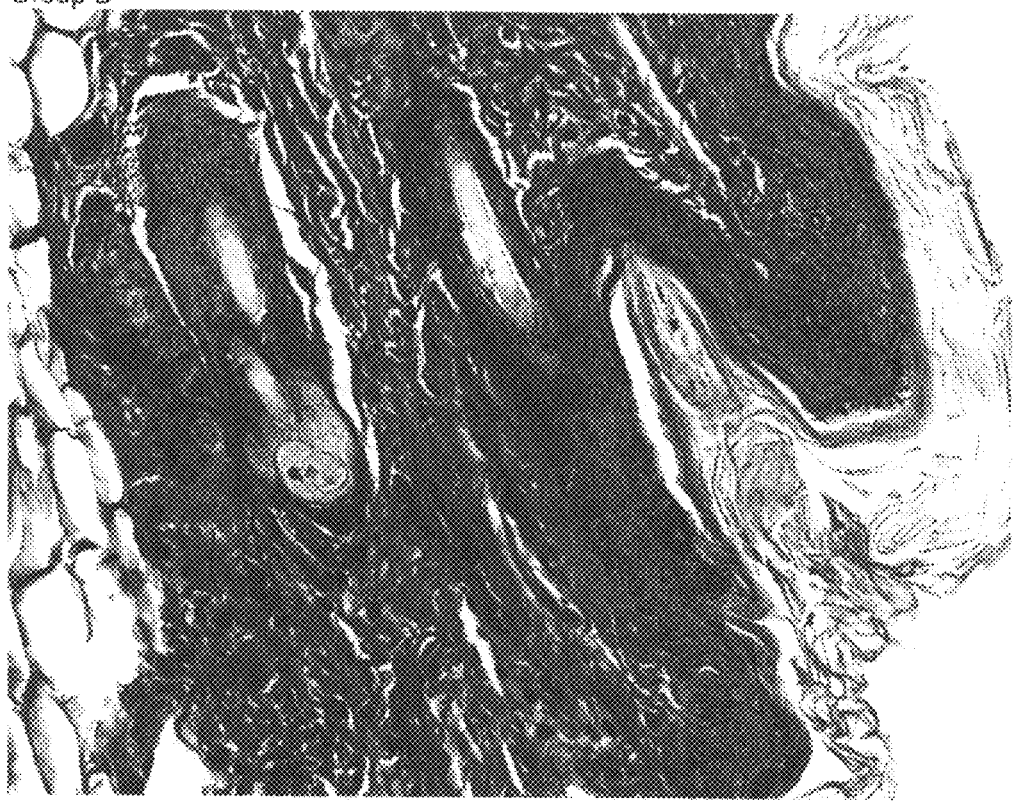

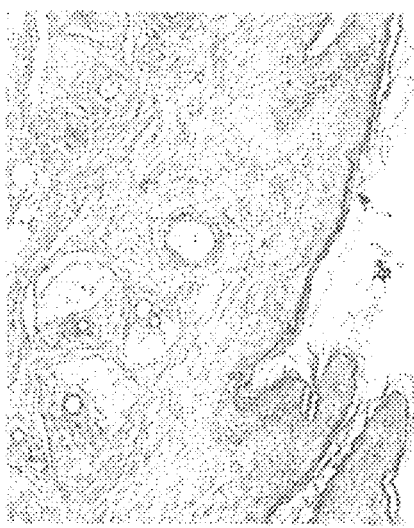
(A)
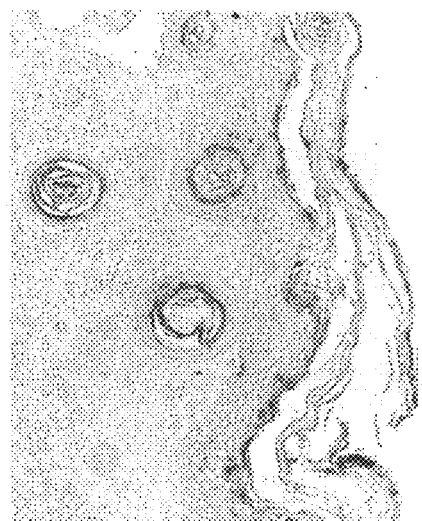
(B)
FIG. 2

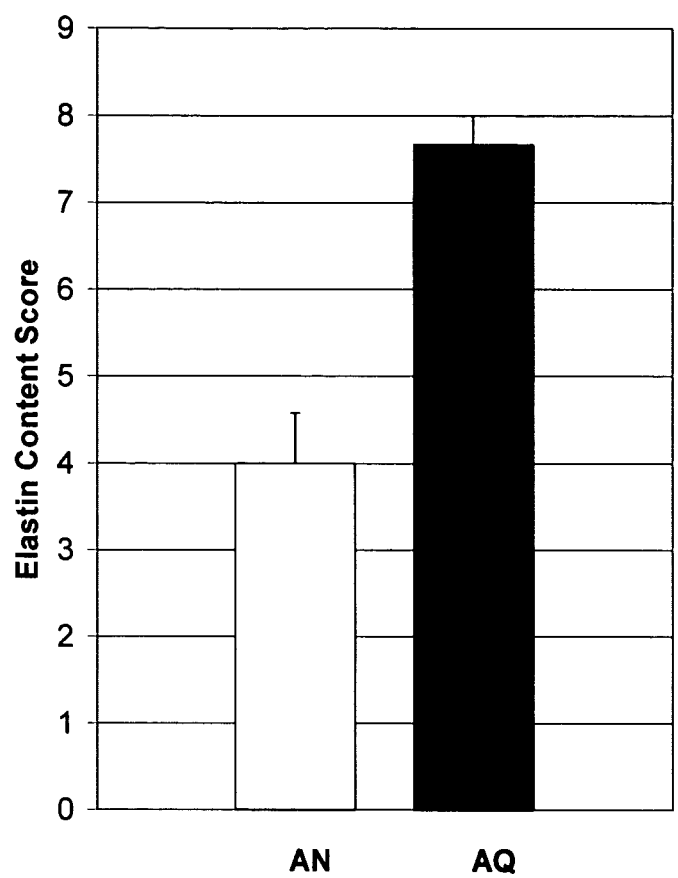
Fig. 4 (AN - control; AQ - containing zinc)

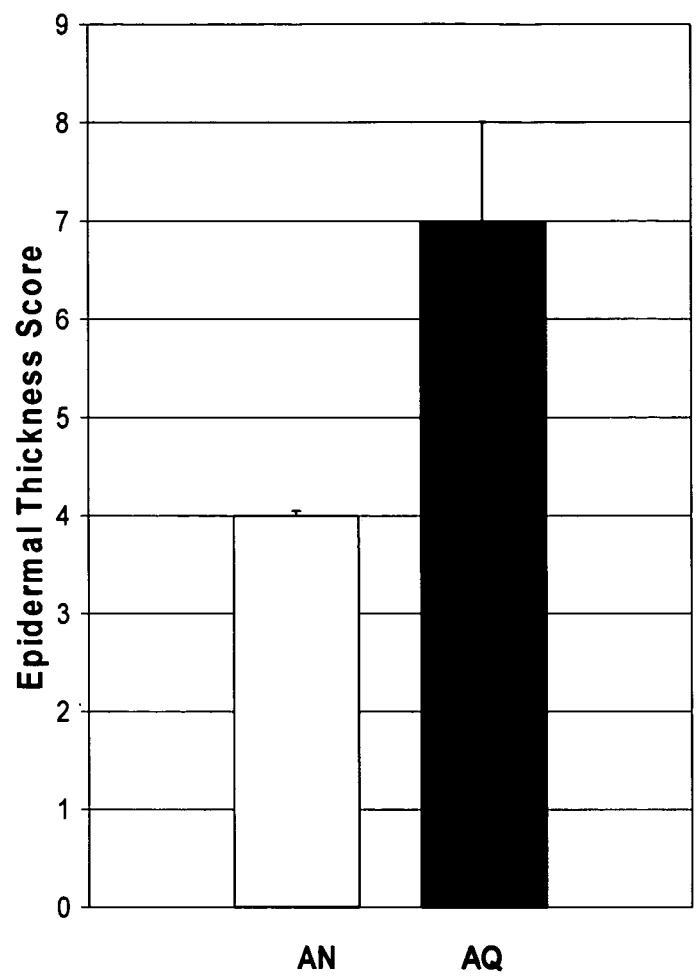
FIG. 5 (AN - control; AQ- containing zinc)

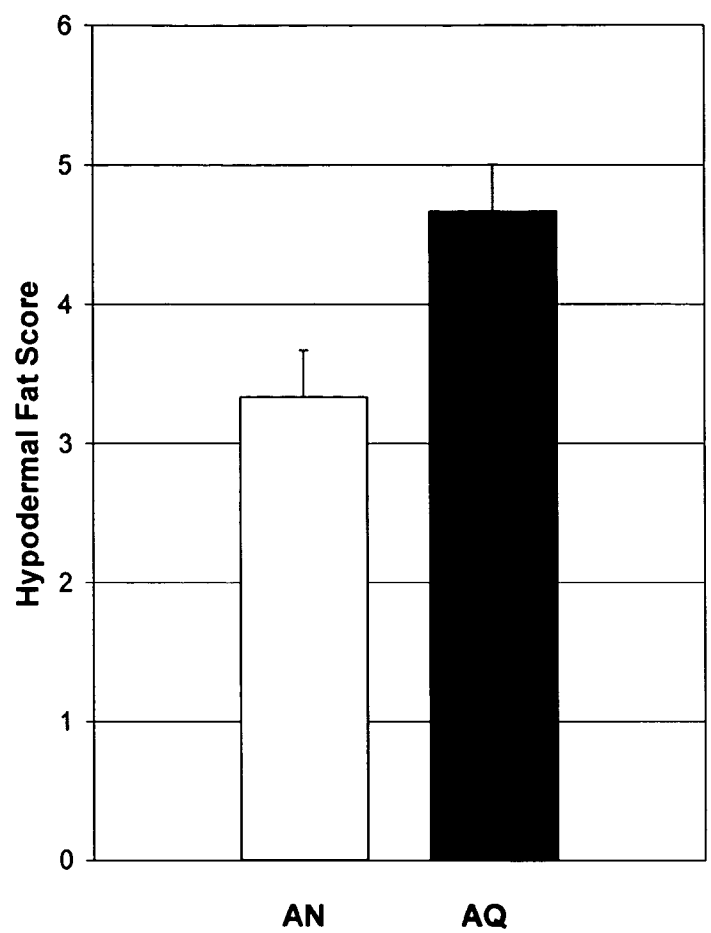
FIG. 6 (AN - control; AQ - containing zinc)

FIG. 7: subject 1 (left image - 0 time; right image - 4 weeks)
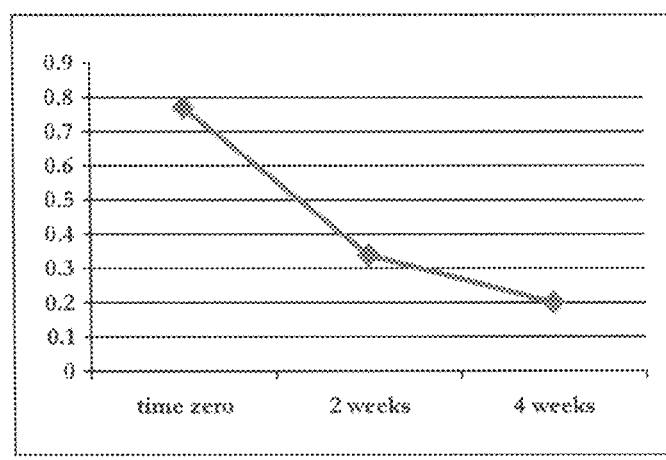

FIG. 8: Subject 2 (left image - time 0; right image - 5 weeks)
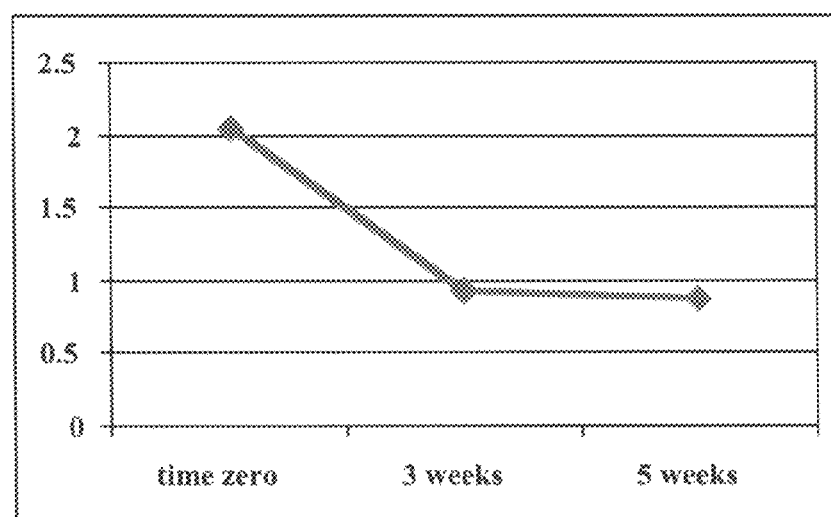
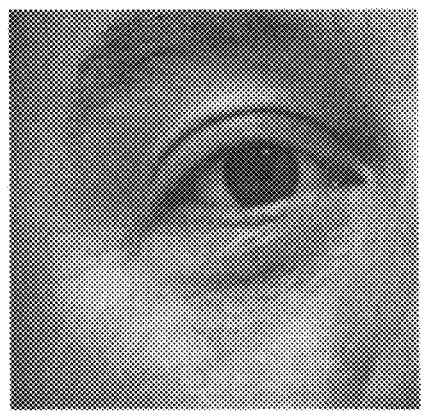
Time Zero
Time 5 Weeks FIG. 9: Subject 3 (left image - time 0; right image - 6 weeks)
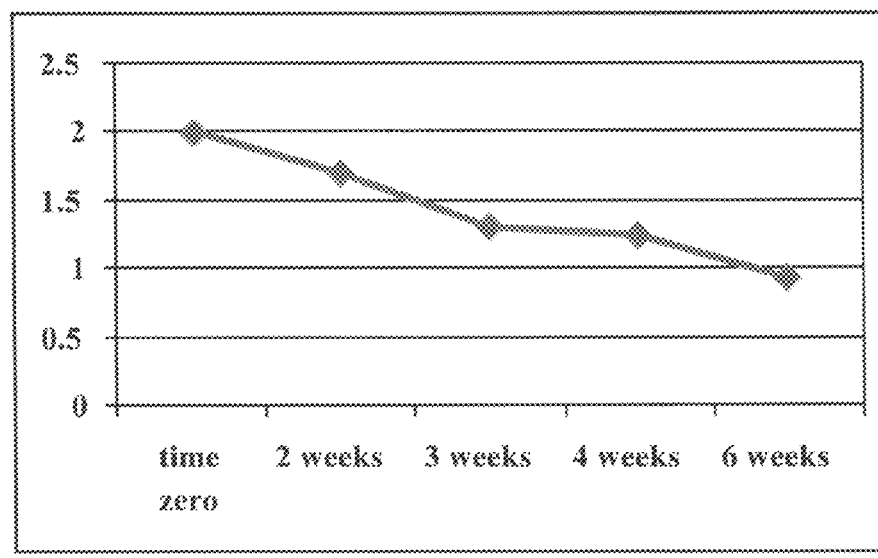
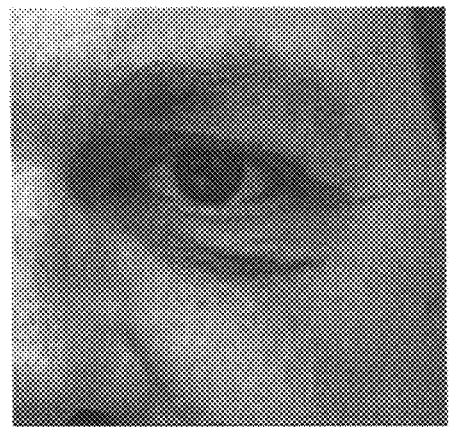
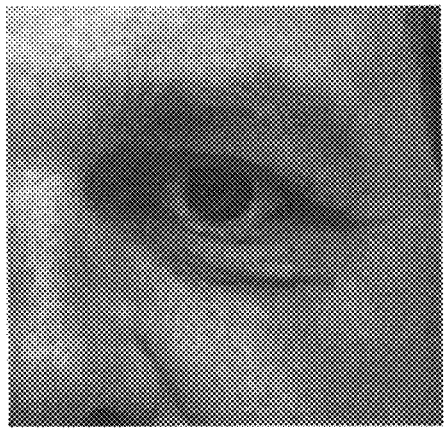

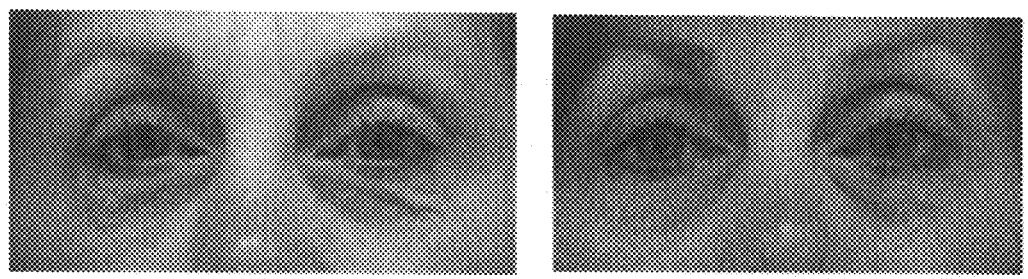
FIG. 10: Subject 4 (left image - time 0; right image - 2 weeks)

FIG. 11: Subject 5 (left image - time 0; right image - 4 weeks)
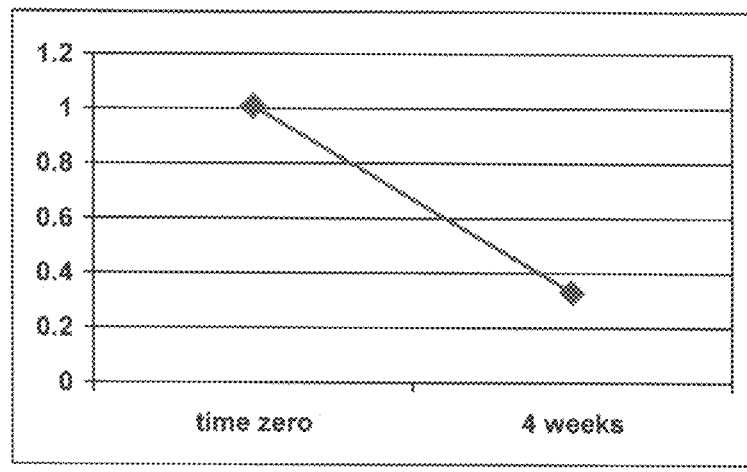

MODULATION OF ZINC LEVELS TO IMPROVE TISSUE PROPERTIES

CROSS-REFERENCES TO RELATED APPLICATIONS

This Application claims priority from U.S. provisional patent application 60/421,278 filed Oct. 25, 2002, entitled "Implantable Medical Devices Using Zinc" and U.S. provisional patent application 60/421,336 filed Oct. 25, 2002, entitled "Modulation of Zinc Levels to Improve Tissue Properties". This application is also related to U.S. non-provisional application entitled "Implantable Drug Devices Using Zinc", of the same inventors filed on the same day herewith. The entire contents of all said applications are hereby incorporated herein.

BACKGROUND OF THE INVENTION

This invention relates to the use of zinc-containing compositions for pharmaceutical and cosmeceutical purposes.

Zinc is one of the most important trace elements in human health and nutrition and plays a significant role in the function of many intracellular proteins. Zinc is crucial for gene expression and nucleic acid metabolism, which accounts in part for its importance in cellular growth and differentiation. Recent investigations indicate that zinc may actually have a regulatory role. Zinc possesses ligand-binding properties that are utilized effectively at the catalytic site of a broad range of enzymes. In addition, it has many structural roles in biological membranes [Tang et al., (2001) *J Nutr* 131: 1414-14200], cell receptors, and proteins (i.e. transcription factors and proteins involved in DNA replication). Zinc has been shown to have an effect on epidermal growth factor (EGF)-stimulated intracellular signaling [Wu et al., (1999) *Am J Physiol* 277: L924-L931] and numerous studies also indicate that zinc possesses insulin-like effects [Tang et al., supra]. Zinc has also been shown to cause an increase in IGF-I and TGF-beta 1 in femoral-diaphyseal and metaphyseal tissue cultures [Ma et al. (2001) *Int J Mol Med* 8(6): 623-8].

Studies have shown that zinc has an effect on epidermal growth factor (EGF) stimulated signaling. Addition of 0.3 mM of zinc or epidermal growth factor resulted in a marked increase in tyrosine phosphorylation of proteins in whole cell extracts [Hansson et al. (1996) *Arch Biochem and Biophys* 328 (2): 233-238]. Zinc has been found to be a potent inhibitor of protein tyrosine phosphatase (PTPase) [Wang et al. (1992) *J Biol Chem* 267(23): 16696-16702], which may induce increased protein tyrosine phosphorylation and generate activation of a host of intracellular signaling that includes MAP kinase activity [Hansson et al., supra]. A wide range of integrated biological responses has been associated with EGFR signaling. These biological responses include mitogenesis, apoptosis, enhanced cell motility, protein secretion, and differentiation or dedifferentiation even on the same cell, depending on the phenotype [Wells (1999) *EGF receptor. Int J Biochem Cell Biol* 31(6): 637-643]. EGFR signaling in adult animals has been postulated to play a role in organ repair and experimental results indicate that EGFR inhibition affects epithelial cell proliferation and stratification. Furthermore, EGFR may also affect wound healing and play a role in maintaining normal epithelial thickness [Nakamura et al. (2001) *Exp Eye Res* 72(5): 511-517]. In a number of patents and publications, zinc has been implicated to play a role in increasing wound healing, and the EGFR signaling pathway may be a key to its ability to help repair wounds.

Zinc has the potential to exert insulin-like effects with respect to lipogenesis [Coulston et al. (1980) *Diabetes* 29(8): 665-667], glucose transport and glucose oxidation in rat epididymal adipocytes [Shisheva et al. (1992) *Diabetes* 41(8): 982-988; May et al. (1982) *J Biol Chem* 257(8): 4362-4368]. Moreover, zinc also potentiates the mitogenic signaling of insulin [Kiss et al. (1997) *FEBS Lett* 415(1): 71-74]. Evidence points out that zinc may actually be involved in several steps of the insulin-signaling pathway. Zinc has been reported to exert positive effects on insulin synthesis and secretion and also is required for structural conformation of insulin [Chausmer et al. *J Am Coll Nutr* 17: 109-115]. In adipocytes, zinc has been shown to stimulate insulin-specific binding through an unknown mechanism [Gomot et al. (1992) *Biol Trace Elem Res* 32: 331-335; Herington (1985) *Horm Metab Res* 17: 328-332]. As mentioned above, zinc also possesses the ability to inhibit PTPase activity. PTPase is an early and critical juncture in insulin signaling. Membrane-associated PTPase activity antagonizes the effects of the insulin receptor and other growth factor-associated tyrosine kinases [Kremerskothen et al. (1993) *Mol Cell Biochem* 125: 1-9; Li et al. (1997) *Endocrinology* 138: 2274-2279; Samet et al. (1999) *Am J Respir Cell Mol Biol* 21: 357-364]. There are several branch points in the insulin-signaling pathway. One of these branch points involves the activation of phosphatidylinositol 3-kinase (PI 3- kinase). PI 3-K is well known to be necessary for the recruitment of GLUT4 to the cell surface. Specific isoforms of protein kinase C (PKC) appear to be necessary for the redistribution of GLUT 4 from intracellular storage sites to the plasma membrane [Braiman et al. (1999) *Mol Endocrinol* 13: 2002-2012; Kanoh et al. (2000) *J Biol Chem* 275: 16690-16696; Standaert et al. (1999) *J Biol Chem* 274: 25308-25316.]. PKC membrane localization and activity can be stimulated by zinc [Csermely et al. (1988) *J Biol Chem* 263: 6487-6490; Forbes et al. (1990) *Biochem Int* 22: 741-748; Forbes et al. (1990) *Biochim Biophys Acta* 1053: 113-117; Quest et al. (1992) *J Biol Chem* 267: 10193-10197]. Recent evidence has shown that zinc may regulate the Ser/Thr protein kinase termed mammalian target of rapamycin or mTOR (also known as FRAP and RAFT) [Lynch et al. (2001) *Am J Physiol Endocrinol Metab* 281(1): E25-E34]. The mTOR signaling pathway begins at the PI 3- kinase activation site. A downstream target of the mTOR pathway is the 40 S ribosomal protein S6, which is a substrate of $p70^{S6k}$ [Lynch, supra]. Amino acids increase mRNA translation (independently of merely serving as substrates for synthesis) through ribosomal protein S6 kinase [Patti et al. (1998) *J Clin Invest* 101(7): 1519-1529]. The 70 kDa ribosomal S6 kinase ($p70^{S6K}$) is an important regulator of cellular translational capacity due to its ability to phosphorylate the 40 S ribosomal protein S6 and regulate 5'-terminal oligopyrimidine tract mRNAs [Martin et al. (2001) *J Biol Chem* 276(11): 7884-7791]. The activation of ribosomal protein S6 therefore up-regulates ribosome biosynthesis and enhances the translational capacity of the cell. Additionally, ribosomal protein S6 has been implicated in the regulation of cell size [Martin et al., supra].

Insulin-like growth factor-I (IGF-I) and transforming growth factor beta-1 (TGF-β1) play important roles in the biological system. The effect of zinc on IGF-I and TGF-β1 production was investigated to determine the role of this metal on growth of growth in newborn rats [Ma, supra]. The results of the experiments showed that the presence of zinc caused a significant increase in protein, IGF-I and TGFβ1 concentrations in medium cultured with diaphyseal or metaphyseal tissues. In addition, expression levels of IGF-I and TGF-β1 were also significantly increased in the diaphyseal and metaphyseal tissues cultured with zinc. Transforming growth factor betas are multifunctional polypeptide growth factors that are involved in proliferation and differentiation of cells, embryonic development, wound healing and angiogenesis [Blobe et al. (2000) *N Engl J Med* 342(18): 1350-1358]. Usually, TGF-beta1 is bound to the extracellular matrix, and can be released by proteases [Taipale et al. (1992) *J Biol Chem* 267: 25378-25384]. The presence of extracellular matrix has been found to down regulate the expression of the TGF-beta1 gene [Streuli et al. (1993) *J Cell Biol* 120: 253-260]. Therefore, TGF-beta may act as a feedback regulator of extracellular matrix formation. TGF-β regulates cellular processes through binding to high-affinity membrane receptors, which causes the assembly of a receptor complex that phosphorylates the proteins of the SMAD family [Blobe et al., supra]. SMADs act as signal transducers of TGF-β family members. After phosphorylation, SMADs form a complex and move into the nucleus and assemble complexes that directly control gene expression through DNA binding and recruitment of transcriptional co-activators or co-repressors [Massague J. (2000) *Nat Rev Mol Cell Biol* 1(3): 169-178]. SMADs help to regulate a number of genes including those for collagen [Zhang et al. (2000) *J Biol Chem* 275(50): 39237-39245] and regulation of SMADs is achieved in several different ways. Once in the nucleus, the activated SMAD complex may activate or repress gene expression. SMADs may bind to p300 (co-activator) or TG3-interacting factor (TGIF) (co-repressor) depending on their relative levels in a cell [Massague, supra]. Evidence suggests that TGIF may set the maximal level to which TGF-β signaling can activate transcription [Wotton et al. (1999) *Cell* 97(1): 29-39]. Signaling through the extracellular-signal-regulated kinase (ERK) increases TGIF levels [Lo et al. (2001) *EMBO J* 20(1-2): 128-136.]. ERK is a member of the mitogen-activate protein kinase (MAPK) pathway, which may be activated through activation of the EGF receptor pathway.

Zinc also has been shown to inhibit aggregation of platelets, particularly in a combined effect with plasma, and specifically with fibrinogen [Chvapil et al. (1975) *Life Sciences* (16): 561-572; Sauvage et al., U.S. Pat. No. 5,401,730].

Elastin is a resilient connective tissue protein present in the extracellular matrix and is especially abundant in tissues that undergo repeated physical deformations, i.e. lungs, blood vessels and skin [Parks (1997)]. Posttranscriptional regulation of lung elastin production. *Am J Respir Cell Mol Biol* 17: 1-2]. Elastin is a polymer composed of enzymatically cross-linked tropoelastin, which is the secreted soluble precursor protein [Zhang et al. (1999) *Mol Cell Biol* 9 (11): 7314-7326]. Similar to other structural extracellular matrix proteins, the majority of elastin production is restricted to a narrow window of development. In the majority of tissues, elastogenesis increases dramatically during late fetal life, peaks near birth and early neonatal life, decreases significantly soon after and is nearly repressed by maturity. Previous investigations have shown that insulin-like growth factor-I (IGF-I) increased elastin gene transcription through displacement of protein binding to the proximal promoter. Sp 1 and Sp3 have been identified as factors whose binding is abrogated by IGF-I [Conn et al. (1996) *J Biol Chem* 271(46): 28853-28860]. At the post-transcriptional level, TGF-β increases elastin gene expression through increasing the stability of tropoelastin mRNA [Kahari et al. (1992) *Lab Invest* 66(5): 580-588]. Zinc affects IGF-I and TGF-β expression, which suggests that zinc may increase elastin production through these two proteins. After tropoelastin synthesis, a 67 kDa elastin binding protein binds it and acts as an effective chaperone, preventing its premature intracellular aggregation [Hinek et al. (1994) *J Cell Biol* 126(2): 563-574]. Tropoelastin and the elastin binding protein remain bound until the complex is excreted into the extracellular space where the chaperone interacts with galactosugars of the microfibrils, decreasing its affinity for the tropoelastin molecule. Microfibrillar components act as scaffolds for the deposition of elastin. Once the tropoelastin molecules are properly aligned, they are cross-linked by lysyl oxidase [Robert (1999) *Connect Tissue Res* 40 (2): 75-82]. A combination of ascorbic acid, tyrosine, and zinc sulfate applied to the skin has been shown to produce a readily observable diminution of the fine wrinkle structure [Schinitsky et al., U.S. Pat. No. 4,938,969]. The mechanism was not clearly understood, but the patent states that the three ingredients were believed to function in cooperation to stimulate fibroblast proliferation and to promote their production of collagen and elastin, thereby promoting the supporting role of the associated dermal tissue (col. 2 lines 12-16).

Other patents disclose beneficial effects of certain zinc compounds when combined with other active agents on skin. Thornfeldt, U.S. Pat. No. 6,071,543 discloses combinations of salts of pyridinethiol oxides and combinations of such salts with metal oxides and thiols, to treat or prevent signs of aging in skin or mucous membranes. Specific combinations mentioned include zinc pyrithione with selenium pyrithione and zinc pyrithione with selenium sulfide. Perricone, U.S. Pat. No. 5,554,647 includes a discussion of the use of zinc (for example, in the form of zinc sulfate) as a secondary ingredient in compositions for treatment of aging skin, where the primary active ingredient in the compositions is an acetylcholine precursor. The zinc is said to be effective for enhancement of neurotransmitter synthesis. Murad, U.S. Pat. No. 5,972,999, discloses compositions for skin treatment whose primary active ingredient is one or more sugar compounds that are converted into glycosaminoglycans in the bloodstream. These compositions may also include a zinc component, preferably zinc complexed with an amino acid such as methionine. Such zinc compounds are said to assist in some way in binding collagen and elastic tissue in order to rebuild damaged or aged skin.

BRIEF DESCRIPTION OF THE DRAWINGS

FIG. 2 depicts photomicrographs of murine skin sectioned and stained, treated with a composition containing zinc, and a control, demonstrating tropoelastin content.

FIGS. 4-6 are graphical depictions of comparative scores for elastin content, epidermal thickness and hypodermal fat, for a composition of the invention as compared to a control.

FIGS. 7-11 are depictions of test results on increase in skin elasticity by surface application of compositions of the invention, using graphs and photographs.

SUMMARY OF THE INVENTION

Figure 1B:
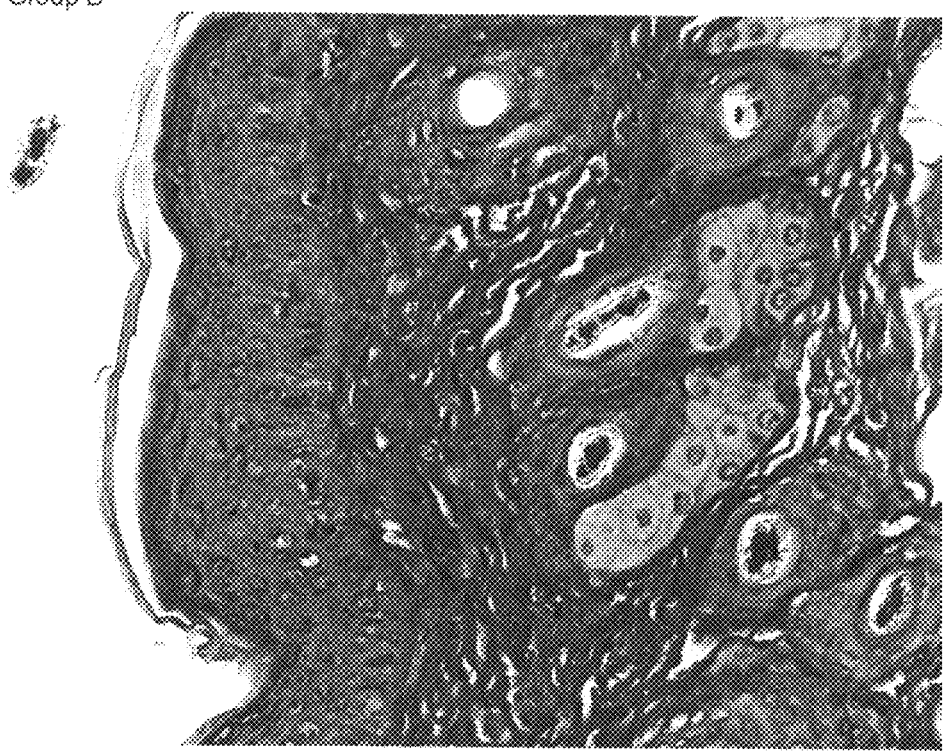
FIGS. 1(*a*) -1(*d*) depict photomicrographs of murine skin sectioned and stained, treated with varying concentrations of zinc ion to increase elastin content.
Figure 1C:

The present invention relates to zinc-containing compositions and methods, particularly topical methods, which are employed to achieve one or more of several effects, including increasing or decreasing epidermal thickness, increasing elasticity or elastin levels, and increasing or decreasing fat in or near the skin. While we do not wish to be bound thereby, it is believed that these formulations and methods provide such results by supplying increased local ionic zinc concentrations to the relevant tissues.

In general, the invention comprises a method for altering the properties of tissue of a subject, said altering being selected from the group consisting of increasing fat content in said tissue, decreasing fat content in said tissue, increasing epidermal thickness, decreasing epidermal thickness, and increasing elastin content in said tissue, said method comprising applying a dermatologically or pharmaceutically acceptable composition consisting essentially of one or more zinc-containing components (e.g. zinc compounds, complexes and/or chelates) in admixture with a dermatologically or pharmaceutically acceptable carrier, in an effective tissue-modifying amount to one or more sites on said tissue in need of said modifying.

More specifically, in one aspect the invention comprises a method for increasing fat production in the skin (i.e., "superficial fat") or beneath the skin (i.e., "deep fat") of a subject, which comprises topically applying a dermatologically or pharmaceutically acceptable composition consisting essentially of one or more zinc-containing components in admixture with a dermatologically or pharmaceutically acceptable carrier, in an amount effective to increase fatty tissue, to a site on the subject in need of increased fat. In another aspect the invention comprises a method for decreasing fat production in or beneath the skin, which comprises topically applying a dermatologically or pharmaceutically acceptable composition consisting essentially of one or more zinc-containing components in an amount effective to decrease fatty tissue to a site on the subject in need of decreased fat. By increasing or decreasing fatty tissue is meant to increase or decrease the mass of fatty tissue, which may be done by affecting either the number of adipocytes or the size of individual existing adipocytes. In a third aspect the invention comprises a method for increasing elastin content in a tissue of a subject (including but not limited to the skin), which comprises topically applying to said tissue a dermatologically or pharmaceutically acceptable composition consisting essentially of one or more zinc-containing components in admixture with a dermatologically or pharmaceutically acceptable carrier in an effective elastin-increasing amount. A fourth aspect of the invention comprises a method for increasing epidermal thickness in a subject, the method comprising topically applying a dermatologically or pharmaceutically acceptable composition consisting essentially of one or more zinc-containing components in admixture with a dermatologically or pharmaceutically acceptable carrier in an effective epidermal thickness-increasing amount, to an area of the skin of the subject in need of increased epidermal thickness. In another aspect, the invention comprises a method for decreasing epidermal thickness in a subject, which comprises topically applying a dermatologically or pharmaceutically acceptable composition consisting essentially of one or more zinc-containing components in admixture with a dermatologically or pharmaceutically acceptable carrier to an area of the skin of the subject in need of decreased epidermal thickness.

Yet another aspect of the invention comprises a method for increasing elastin content of the lens of an eye of a subject comprising placing over the lens a contact lens comprising one or more zinc-containing components, whereby the contact lens releases zinc ions onto the locus of the lens of the eye and/or adjacent tissues (such as muscles) in an effective elastin-increasing amount. Such a lens, itself, also comprises an aspect of this invention.

In other aspects, the invention comprises dermatologically and/or pharmaceutically acceptable compositions for the above methods and purposes, containing, or consisting essentially of, an amount of one or more zinc-containing components effective for the purpose in question, and also comprising one or more dermatologically and/or pharmaceutically acceptable carriers.

DETAILED DESCRIPTION OF THE INVENTION

As described briefly above, the invention comprises methods and compositions for providing zinc, which may be in the form of zinc ions, to a selected site or portion of a subject's body in order to achieve a favorable result of the type described herein. A number of different results are contemplated herein, including increasing or decreasing fat content in skin or other tissues, increasing or decreasing epidermal thickness, and increasing elastin content. In general, as described in more detail below, compositions containing one or more zinc-containing components are applied, usually topically, to a site or location on the subject's body that is deemed to be in need of one or more of the said results. By "in need" is meant both pharmaceutical or health-related needs, for example, healing or restoring tissue, as well as cosmetic needs, for example, altering or improving the appearance of tissue.

Compositions of the present invention are useful for regulating signs of skin aging, particularly visible and/or tactile discontinuities in skin texture associated with aging. "Regulating the signs of skin aging" includes prophylactically regulating and/or therapeutically regulating one or more of such signs (similarly, regulating a given sign of skin aging, e.g., lines, wrinkles or pores, includes prophylactically regulating and/or therapeutically regulating that sign). As used herein, prophylactically regulating such signs includes delaying, minimizing and/or preventing signs of skin aging. As used herein, therapeutically regulating such signs includes ameliorating, e.g., diminishing, minimizing and/or effacing signs of skin aging.

By "signs of skin aging" is meant outward visibly and tactilely perceptible manifestations as well as other macro or micro effects due to skin aging. These signs include the development of textural discontinuities such as wrinkles, including both fine superficial wrinkles and coarse deep wrinkles, skin lines, crevices, bumps, large pores, scaliness, flakiness and/or other forms of skin unevenness or roughness, loss of skin elasticity, sagging (including puffiness in the eye area and jowls), loss of skin firmness, loss of skin tightness, loss of skin recoil from deformation, discoloration (including undereye circles), blotching, sallowness, hyperpigmented skin regions such as age spots and freckles, keratoses, abnormal differentiation, hyperkeratinization, elastosis, collagen breakdown, and other histological changes in the stratum corneum, dermis, epidermis, the skin vascular system (e.g., telangiectasia or spider vessels), and underlying tissues, especially those proximate to the skin.

Such signs may be induced or caused by intrinsic factors or by extrinsic factors, e.g., chronological aging and/or environmental damage or other pathological state. It should be noted, however, that in this embodiment the present invention is not limited to regulation of the above-mentioned signs of skin aging that arise due to mechanisms that are associated with skin aging, but is intended to include regulation of said signs irrespective of the mechanism of origin.

Compositions, devices and methods of this invention are useful for therapeutically regulating visible and/or tactile discontinuities in mammalian skin texture, including texture discontinuities related to skin aging. This includes ameliorating, e.g., diminishing, minimizing and/or effacing visible and/or tactile discontinuities in the texture of mammalian skin, to thereby provide improved skin appearance and/or feel, e.g., a smoother, more even appearance and/or feel. For example, the length, depth, and/or other dimension of lines and/or wrinkles may be decreased, the apparent diameter of pores may decrease, or the apparent height of tissue immediately proximate to pore openings may decrease so as to approach that of the interadnexal skin.

The present invention is also useful for prophylactically regulating visible and/or tactile discontinuities in mammalian skin texture, including texture discontinuities associated with skin aging, that is, delaying, minimizing and/or preventing visible and/or tactile discontinuities in the texture of skin, to thereby provide improved skin appearance and/or feel, e.g., a smoother, more even appearance and/or feel.

Compositions of this invention contain one or more zinc-containing components that are effective in carrying out the purposes. The particular zinc-containing component or components employed, and the concentration in the compositions, can depend on the purpose for which the composition is to be applied.

In general, the zinc-containing components used in this invention include ingredients such as compounds, complexes, chelates, etc. of zinc. Among zinc compounds, particularly useful in the compositions and methods of this invention are zinc salts, including acetate, ascorbate, aspartate, butyrate, caproate, caprylate, carbonate, chromate, citraconate, citramalate, citrate, EDTA, formate, fumarate, gallate, gluconate, halides, iodate, lactate, laurate, laureate, malate, maleate, malonate, metaphosphate, methanesulfonate, monophosphate, myristate, nitrate, octoate, oleate, orotate, orthophosphate, oxalate, oxides, palmitate, permanganate, phenolsulfonate, phosphate, picolinate, propionate, pyrophosphate, salicylate, selenate, stearate, succinate, sulfate, sulfonate, tannate, tartrate, tetrametaphosphate, titanate, transferrin, tripolyphosphate, undecylate, and valerate. Also, usable in the invention are chelates of zinc and other types of zinc-containing chemical substances such as complexes, for instance complexes of zinc with amino acids such as methionine or nucleotide-based carriers and the like.

The compositions of this invention are preferably in the form of products to be applied to the skin, gums, eyes, or other tissues of humans or other mammals. They therefore contain a dermatologically or pharmaceutically acceptable carrier, vehicle or medium, i.e. a carrier, vehicle or medium that is compatible with the tissues to which they will be applied. The term "dermatologically or pharmaceutically acceptable," as used herein, means that the compositions or components thereof so described are suitable for use in contact with these tissues or for use in patients in general without undue toxicity, incompatibility, instability, allergic response, and the like.

In addition, compositions of the invention may comprise any ingredient conventionally used in the fields under consideration, and particularly in cosmetics and dermatology.

The term "effective amount" as used herein means an amount of a compound or composition according to this invention that is sufficient to significantly induce a particular positive benefit, but that implicitly is a safe amount, i.e. one that is low enough to avoid serious side effects. The positive benefit may be health-related, or it may be more cosmetic in nature, or it may be a combination of the two.

In terms of their physical form, compositions of this invention may include solutions, emulsions (including microemulsions), suspensions, creams, lotions, gels, powders, or other typical solid or liquid compositions used for treatment of skin, gums, eyes, etc. Such compositions will contain, in addition to the zinc salts of this invention, other ingredients typically used in such products, such as antimicrobials, moisturizers and hydration agents, penetration agents, preservatives, emulsifiers, natural or synthetic oils, solvents, surfactants, detergents, gelling agents, emollients, antioxidants, fragrances, fillers, thickeners, waxes, odor absorbers, dyestuffs, coloring agents, powders, viscosity-controlling agents and water, and optionally including anesthetics, anti-itch actives, botanical extracts, conditioning agents, darkening or lightening agents, glitter, humectants, mica, minerals, polyphenols, silicones or derivatives thereof, sunblocks, vitamins, and phytomedicinals.

In addition to zinc-containing components, the compositions may contain other active ingredients used in skin or dental care. For instance, they may contain anti-acne actives; anti-wrinkle, anti-skin atrophy or skin repair actives; skin barrier repair actives; non-steroidal cosmetic soothing actives; artificial tanning agents and accelerators; sunscreen actives; sebum stimulators; sebum inhibitors; anti-oxidants; protease inhibitors; skin tightening agents; anti-itch ingredients; desquamating enzyme enhancers; anti-glycation agents; and mixtures of such actives.

Compositions according to this invention may be in the form of controlled-release or sustained-release compositions, wherein the zinc-containing component or components is encapsulated or otherwise contained within a material such that it is released into the surrounding environment (e.g. skin or other tissue) in a controlled manner over time. The zinc-containing component or components may be contained within matrixes, liposomes, vesicles, microcapsules, microspheres and the like, or within a solid particulate material, all of which is selected and/or constructed to provide release of the zinc-containing component over time. The release-controlling material may be biodegradable or non-biodegradable, and may be applied per se or in the form of a composition such as an emulsion, suspension, cream, ointment, etc.

The compositions of the invention preferably are formulated so that they contain an amount of one or more zinc-containing components that is effective per se in obtaining the desired effect or result, as described below, so that this desired effect can be obtained with a single application, or with a relatively small number of repeated applications. In general, the compositions of this invention typically contain a total concentration of the zinc-containing component or components that is from about 1.0 picomolar (pM) to about 100 millimolar (mM). The compositions are applied over a period of time, and in a number of applications, so as to achieve the particular objective desired. In some cases the ranges over which particular effects occur are different while in others (for instance in the case of fat alteration and elastin deposition) an overlap exists. The examples herein contain guidance of the effects obtained by using different concentrations of zinc compounds or complexes and varying frequencies and lengths of application of the compositions. If one effect is desired, a concentration at which that effect predominates would be selected. An interesting range for topical application is one that accomplishes epidermal thickening and increases elastin content together with either an increase in fat content or no decrease in fat content. To achieve this goal, the ranges and durations of topical applications in the examples may be used. In some cases the application of such a composition will be carried out by or under the supervision of a dispensing physician, chiropractor or other health care professional, who will be responsible for ensuring that the proper amount of the composition is used to achieve the desired effect.

Elasticity and Elastin.

In one aspect, the invention provides methods, compositions and devices for improving tissue elasticity or increasing elastin levels. In one embodiment the invention comprises a method for increasing elastin content in a tissue of a subject (including but not limited to the skin), which comprises topically applying to said tissue a dermatologically or pharmaceutically acceptable composition consisting essentially of one or more zinc-containing components in an effective elastin-increasing amount in admixture with at least one dermatologically or pharmaceutically acceptable carrier. This application is particularly relevant for increasing skin elasticity or elastin levels either to reverse aging-related or other undesirable changes or to provide a cosmetic improvement.

Areas of the skin to which the compositions may be applied include the face (including cheeks, peri-eye, circum-oral, forehead, lips and peri-nose), breasts, buttocks, neck, arms, legs, torso, or furrows or wrinkles in the face, hands and neck.

For improving elastin or elasticity in the skin, a composition according to this invention contains one or more zinc-containing components in a total concentration of from about 1.0 picomolar (pM) to about 900 µM, preferably from about 100 to about 500 pM. The composition may be applied topically so as to provide an effective amount of zinc to the area where the effect is desired, and may be applied at varying intervals and over varying durations to achieve the desired degree of increase in elastin content.

In another embodiment of the invention, a contact lens, preferably a hard lens, coated with one or more zinc-containing components is employed for the purpose of altering the elasticity of the lens of the eye so as to change its shape and/or render it more elastic. Such application may be carried out alone or in conjunction with other treatments that are aimed at improving vision, for example treatments to diminish presbyopia. Coating the lens may be done, for instance, using techniques mentioned in U.S. Pat. Nos. 6,113,636, 6,190,407, 6,267,782 and 6,322,588. The contact lens could be treated with a plasma discharge so that the outer margins of its inner surface would be derivatized (for example with vaporized allylamine). This reactive surface, which would contact the outer margins of the lens when properly used, would then be linked to a chelator of variable affinity for zinc ions, preferably one having 6 or more carbon atoms for controlled release of ionic zinc (for example, undecylenate). This linkage either would be carried out in the presence of zinc ions or would be followed by loading of the contact with ionic zinc prior to administration. Alternatively, the zinc-containing coating may first be applied to the material from which the lens will be made, as discussed generally in these patents.

In this embodiment, the contact lens would produce transient reshaping of the lens of the eye, and the ionic zinc would induce elastin production in that lens to confer elasticity for the corrected shape. The lens of the eye would tend to retain the corrected shape even after removal of the contact lens. Treated contact lenses for this embodiment of the invention preferably produce local ionic zinc concentrations from 0.1 to 100 micromolar in the vicinity of the lens. Within the effective range, lower concentrations of zinc may be used over longer periods of time to achieve the same result, or higher concentrations may be used for shorter periods. Generally, the zinc concentration may range from about 1.0 pM to about 500 mM of the zinc-containing component or components, preferably from about 100 pM to about 50 mM, at the tissue-contact lens interface.

Alteration of Fat Levels.

In another embodiment of the invention, compositions of the invention are applied topically to alter local fat levels either by increasing the fat level or by decreasing it. This alteration of fat level is believed to be due to an alteration of local zinc levels. The fat level affected may be that of the skin itself ("superficial fat") or may be of tissue lying below the skin ("deep fat"). Such application can be made alone or in combination with other factors to either increase or decrease local fat levels. Methods according to the invention for increasing fat provide benefits such as cosmetic benefits in reducing appearance of furrows or deep wrinkles, breast augmentation (contour or size) through topical application, lip augmentation for cosmetic benefit, soft tissue reconstruction or remodeling for cosmetic benefit, or tissue reconstruction of a contour defect to reduce the appearance of the defect, or to provide desired cosmetic or functional effects. Methods for decreasing fat provide benefits such as reduced trunk, leg or other fat stores to decrease apparent weight or improve gross aesthetic contour (e.g., topical pseudo-liposuction), decreased volume of peri-orbital fat (e.g., topical pseudo-blepharoplasty), or lip reduction.

For increasing fat the compositions may be applied to areas of the body such as the lips, soft tissue, furrows or wrinkles in the face, breasts, stretch marks, buttocks, cheeks, arms, and/or legs. For decreasing fat the compositions may be applied to the torso (including the anterior abdomen or belly), isolateral abdomen (commonly known as "love handles"), legs, face, neck, buttocks, arms, legs and eyelids or the peri-eye region.

Compositions for use in this embodiment of the invention for increasing fat content contain one or more zinc-containing components, in a total concentration of from about 1.0 pM to about 900 µM, preferably from about 100 pM to about 500 µM. Compositions for decreasing fat content contain the zinc-containing component or components in a higher total concentration, one of from about 10 µM to about 100 mM, preferably from about 100 µM to about 10 mM.

Changing Epidermal Thickness.

Topical application of a composition according to this invention can be carried out for the purpose of increasing epidermal thickness, for instance, to decrease appearance of fine lines or wrinkles, or to reverse epidermal atrophy from age or various pathologic states. Such applications can be made to appropriate parts of the body, particularly the face (areas adjacent to the eyes, lips or forehead, for example). Conversely, compositions of this invention may be applied to decrease epidermal thickness, for instance, to decrease or eliminate scars and stretch marks. Again, these effects are believed to occur as a result of an alteration of zinc levels in the relevant tissues.

Compositions for increasing epidermal thickness will contain one or more zinc-containing components in a total concentration of from about 1.0 pM to about 900 µM, preferably from about 100 pM to about 500 µM. Compositions for decreasing epidermal thickness will contain a total concentration of from about 10 µM to about 100 mM zinc-containing components, preferably from about 100 µM to about 10 mM.

Gum Treatments.

Compositions of this invention may also be applied topically to the gums, to increase tissue zinc levels in order to prevent or treat gum regression or atrophy. This is believed to result from the effect of the zinc in promoting elastin increase and/or the increase of epidermal tissue, a possible combination of two effects, to better anchor the teeth in place. Compositions for this purpose will contain a total concentration of from about 1.0 pM to about 100 mM, preferably from about 100 pM to about 900 μM, of one or more zinc-containing components.

EXAMPLES

The following examples are provided by way of illustration only and not by way of limitation. Those of skill will readily recognize a variety of noncritical parameters that could be changed or modified to yield essentially similar results.

Example 1

Topical Application of a Zinc Formulation to Increase Skin Elasticity

To achieve a therapeutic benefit for skin elasticity, initial stock solutions were prepared as follows:
Sample Stock Solutions
a) Base only ("blank")
b) 10 μM $Zn^{++}$ ("Z low")
c) 1.0 mM $Zn^{++}$ ("Z med")
d) 100 mM $Zn^{++}$ ("Z high")

To prepare these solutions, a 1.0 M stock of zinc acetate [$ZnAc*(H2O)_2$] (Mallinkrodt Lot 8740 KPRK) was prepared in sterile phosphate buffered saline (PBS, pH 7.2, Gibco BRL Lot #1111327) by dissolving 109.75 g in 500 mL. To 0.2 ml of Cetaphil® moisturizer base was added 20 μl of solution a, b, c, or d depending upon group (corresponding to Groups "A," "B," "C," or "D"). For group A, added 20 μl PBS alone to 180 μl Cetaphil×84 tubes. For group B, added 20 μl 1.0M Zn to 180 μl Cetaphil×84 tubes. For group C, added 200 μl of 1.0M Zn to 19.8 ml PBS, vortexed, labeled as 0.01M Zn, and added 20 μl of 1.0M Zn to 180 μl Cetaphil×84 tubes. For group D, added 200 μl 0.01M Zn to 19.8 ml PBS, vortexed, labeled as 0.1 mM Zn, and added 20 μl 1.0M Zn to 180 μl Cetaphil×84 tubes. After addition of samples to moisturizer base, the samples were mixed to homogeneity and stored at 4° C. overnight. At N=4 per treatment group, C57 Black Six mice at 8 weeks of age were anesthetized with 3% isoflurane by inhalation, and were shaved at mid-scapular dorsal region. Moisturizer was applied daily at 0.2 cc per day for each group for a 21 day period. After 21 days application, the treated skin segment was harvested en bloc and subdivided into three equal portions: a cranial portion, a left lateral portion, and a right lateral portion. The cranial portion and the left lateral portion were fixed in 10% neutral buffered formalin for 12-16 hours, then rinsed in 70% ethanol and embedded in paraffin. The right lateral portion was snap frozen in OCT medium at the time of harvest and stored at −35° C. until use.

Paraffin-embedded specimens were sectioned at 4-6 microns, deparaffinized, and stained with Verhoeff elastica stain for morphological assessment of elastin content. All procedures and analyses were performed by blinded observers. High resolution digital micrographs of each preparation were obtained using a Diagnostic Instruments SPOT camera (Diagnostic Instruments, Sterling Heights, Mich.) as displayed on a Nikon E600 epifluorescence microscope with plan-apochromat lenses. Representative photomicrographs depicting elastin content (black fibers) are depicted as FIGS. 1(a)-1(d).

FIG. 1 depicts representative photomicrographs of murine skin sectioned and stained with Verhoeff Elastica stain after 21 days topical treatment with a) Base only ("blank"), b) 10 μM Zn++ ("Z low"), c) 1.0 mM Zn++("Z med"), or d) 100 mM Zn++("Z high") depicting increasing elastin levels. As the dose of Zn increases from zero (a) to low (b) to medium (c) to high (d) the length, density and thickness of the black elastic fibers increases significantly. At high dose, epidermal sloughing and irritation occurs, however. Lower doses afford the benefits without local signs of irritation. Overall, ionic zinc affords dose-dependant increases in the elastin content of skin after topical administration.

Example 2

Topical Application of a Zinc Formulation to Alter Epidermal Thickness

Paraffin-embedded specimens from animals treated in example 1 above were sectioned at 4-6 microns, deparaffinized, and stained with a combination of Verhoeff elastica stain and the Masson trichrome stain for morphological assessment of epidermal thickness. All procedures and analyses were performed by blinded observers. High resolution digital micrographs of each preparation were obtained using a Diagnostic Instruments SPOT camera (Diagnostic Instruments, Sterling Heights, Mich.) as displayed on a Nikon E600 epifluorescence microscope with plan-apochromat lenses. Images were analyzed using Image Pro Plus software (Media Cybernetics, Silver Spring, Md.) to determine total cross-sectional area of epidermis over standardized lengths. Mean and standard error were assessed using Statview (Abacus Concepts, Berkeley, Calif.), with comparisons made using ANOVA repeated measures and significance determined at 95% with post-hoc testing using Fisher PLSD or Scheffe F-test. Results are presented as Table 1 below.

TABLE 1

Epidermal area (pixels) across standardized epidermal lengths 21 days after treatment with a) Base only ("blank"), b) 10 mM Zn++ ("Z low"), c) 1.0 mM Zn++ ("Z med"), or d) 100 mM Zn++ ("Z high").

| Group | Mean | Std. Error |
|---|---|---|
| Base only ("blank") | 18221.646 | 600.673 |
| 10.0 μM $Zn^{++}$ ("Z low") | 16786.125 | 676.14 |
| 1.0 mM $Zn^{++}$ ("Z med") | 20799.188 | 653.073 |
| 100 mM $Zn^{++}$ ("Z high") | 27365.292 | 890.926 |

Paraffin-embedded specimens from animals were treated in Example 1 except that the doses of 10.0 μM $Zn^{++}$, 1.0 μM $Zn^{++}$, 0.1 μM $Zn^{++}$, and the control were applied for 42 days. Specimens were fixed and embedded as above, sectioned at 4-6 microns, deparaffinized, and stained with a combination of Verhoeff elastica stain and the Masson trichrome stain for morphological assessment of epidermal thickness. All procedures and analyses were performed by blinded observers. High resolution digital micrographs of each preparation were obtained using a Diagnostic Instruments SPOT camera (Diagnostic Instruments, Sterling Heights, Mich.) as displayed on a Nikon E600 epifluorescence microscope with plan-apochromat lenses. Images were analyzed using Image Pro Plus software (Media Cybernetics, Silver Spring, Md.) to determine total cross-sectional area of epidermis over standardized lengths. Mean and standard error were assessed using Statview (Abacus Concepts, Berkeley, Calif.), with comparisons made using ANOVA repeated measures and significance determined at 95% with post-hoc testing using Fisher PLSD or Scheffe F-test. Results are presented as Table 2 below.

TABLE 2

Epidermal area (pixels) across standardized
epidermal lengths 42 days after treatment with
a) Base only ("blank"), b) 10 μM Zn++ ("Z low"),
c) 1.0 μM Zn++ ("Z med"), or d) 0.1 μM
Zn++ ("Z high"). P = 0.0014 by ANOVA repeated measures.

| Group | Mean | Std. Error |
|---|---|---|
| Base only ("blank") | 6728.286 | 143.808 |
| 10 μM Zn$^{++}$ ("Z high") | 7203.875 | 230.472 |
| 1.0 μM Zn$^{++}$ ("Z med") | 7724.190 | 240.195 |
| 0.1 μM Zn$^{++}$ ("Z low") | 6710.000 | 173.975 |

Example 3

Topical Application of a Zinc Formulation to Decrease Fat (Hypodermal Brown Fat)

Paraffin-embedded specimens from animals treated in Example 1 above were sectioned at 4-6 microns, deparaffinized, and stained with a combination of Verhoeff elastica stain and the Masson trichrome stain for morphological assessment of brown adipose tissue area. All procedures and analyses were performed by blinded observers. High resolution digital micrographs of each preparation were obtained using a Diagnostic Instruments SPOT camera (Diagnostic Instruments, Sterling Heights, Mich.) as displayed on a Nikon E600 epifluorescence microscope with plan-apochromat lenses. Images were analyzed using Image Pro Plus software (Media Cybernetics, Silver Spring, Md.) to determine total cross-sectional area of epidermis over standardized lengths. Mean and standard error were assessed using Statview (Abacus Concepts, Berkeley, Calif.), with comparisons made using ANOVA repeated measures and significance determined at 95% with post-hoc testing using Fisher PLSD or Scheffe F-test. Results are presented as Table 3 below (P=0.0001).

TABLE 3

Cross-sectional hypodermal adipose area
(pixels) across standardized epidermal lengths
21 days after treatment with a) Base only ("blank"),
b) 10 mM Zn++ ("Z low"), c) 1.0 mM Zn++
("Z med"), or d) 100 mM Zn++ ("Z high").

| | Mean | Standard Error |
|---|---|---|
| a) Base only ("blank") | 456566.375 | 19714.059 |
| b) 10 μM Zn$^{++}$ (Z low) | 436809.417 | 20948.052 |
| c) 1.0 mM Zn$^{++}$ (Z med) | 377185.833 | 33645.848 |
| d) 100 mM Zn$^{++}$ ("Z high") | 132251.333 | 5078.162 |

Since brown adipose tissue and white adipose tissue respond differently and since different combinations of growth factors alter responses for each, ionic zinc can be applied to either significantly increase or decrease fat area, as illustrated in this and the following example.

Example 4

Topical Application of a Zinc Formulation to Decrease Fat (Deep White Fat)

Stock zinc solutions were prepared as above and diluted in Cetaphil as above to achieve a final concentration of 10 μM Zn$^{++}$ in moisturizer base. After addition to moisturizer base, the samples were mixed to homogeneity and stored at 4° C. overnight. At N=4 per treatment group, C57 Black Six mice at 8 weeks of age were anesthetized with 3% isoflurane by inhalation. Moisturizer was applied daily to the lateral curvature of the abdomen from the ribs to the pelvis centered at the mid-axillary line ("love handles"). Moisturizer was applied at 0.2 cc per day for each group for a 21 day period. After 21 days application the treated skin segment was harvested en bloc full depth and fixed in 10% neutral buffered formalin for 12-16 hours, then rinsed in 70% ethanol and embedded in paraffin.

Paraffin-embedded specimens were sectioned at 4-6 microns, deparaffinized, and stained with a combination of Verhoeff elastica stain and the Masson trichrome stain for morphological assessment of brown adipose tissue area. All procedures and analyses were performed by blinded observers. High resolution digital micrographs of each preparation were obtained using a Diagnostic Instruments SPOT camera (Diagnostic Instruments, Sterling Heights, Mich.) as displayed on a Nikon E600 epifluorescence microscope with plan-apochromat lenses. Images were analyzed using Image Pro Plus software (Media Cybernetics, Silver Spring, Md.) to determine total cross-sectional area of epidermis over standardized lengths. Mean and standard error were assessed using Statview (Abacus Concepts, Berkeley, Calif.), with comparisons made using ANOVA repeated measures and significance determined at 95% with post-hoc testing using Fisher PLSD or Scheffe F-test. Results are presented as Table 4 below (P=0.0001).

TABLE 4

Cross-sectional deep adipose area (pixels)
across standardized epidermal lengths 21
days after treatment with a) Base only ("blank"),
b) 10 μM Zn++ as described. P = 0.0001
by ANOVA repeated measures
(Staview SE, Abacus Concepts, Berkeley, CA)

| | Mean | Standard Error |
|---|---|---|
| a) Base only ("blank") | 29375.425 | 937.893 |
| b) 10 μM Zn$^{++}$ | 73011.321 | 5060.653 |

Example 5

Local Application of a Zinc Formulation to Treat or Prevent Gum Regression

A gel or paste solution is used to release ionic Zn to the gum area. For instance, zinc acetate can be added to an ointment formulation. An example of this mixture would consist of Tween 80, glycerol starch, sterile deionized water and triethanolamine. The most preferred formulation would attain local ionic zinc concentrations of 1 to 100 micromolars. This zinc oral composition would be used to treat gum regression and aid in tooth loss caused by gum disease and age related degeneration of gums. Increased elastin and epidermal tissue would help to anchor the tooth in place and provide support.

Examples 6-8

Examples 6-8 show the effect of the application of a composition according to the invention in (a) increasing tropoelastin content, (b) altering epidermal thickness, elastin content and hypodermal fat, and (c) increasing skin elasticity. Among others, it was found that in general the effects of increasing epidermal thickness, increasing epidermal fat and inducing new elastin production are dose-dependent and that the effective ranges of active ingredients for these three effects overlap.

Example 6

Topical Application of a Zinc Formulation to Increase Tropoelastin Content

A stock zinc solution was prepared as above to achieve a final concentration of 100 micromolar Zn++ in commercial moisturizer bases. After addition to moisturizer bases, the samples were mixed homogeneity and stored at room temperature. At N=3 per group, C57 Black Six mice at 8 weeks of age were anesthesized with 3% isoflurance by inhalation. Moisturizer was applied daily to the dorsal skin of the mouse. Moisturizer was applied at 0.2 cc per day for each group for a 7-day period. After 7-day application, the treated dorsal skin was harvested and divided into three segments. One segment fixed in 10% neutral buffered formalin for 12-16 hours, then rinsed in 70% ethanol and embedded in paraffin. Two segments were frozen and stored at $-73°$ C.

Paraffin-embedded specimens were sectioned at 4-6 microns, deparaffinized, and probed with fluorescein labeled DNA primers to tropoelastin (5'FGCCTGGTGCCCACT SEQ ID NO: 1 and 5'FCTCCACCAAGGCCATA SEQ ID NO: 2) and stained with Fast Red stain. Paraffin-embedded specimens were sectioned at 4-6 microns, deparaffinized, and stained with antibody conjugated to alkaline phosphate and counterstained with Eosin stain. All procedures and analyses were done by blinded observers. High resolution digital micrographs of each preparation we obtained using a Diagnostic Instruments SPOT camera (Diagnostic Instruments, Sterling Heights, Mich.) as displayed on a Nikon E600 epifluoresence microscope with a plan-apochromat lenses. Images were analyzed using Image Pro Discovery software (Media Cybernetics, Silver Spring, Md.) to determine total cross-sectional tropoelastin content. Mean and standard error were assessed using Statview (Abacus Concepts, Berkeley, California), with comparison made using ANOVA repeated measure and significance determined at 95% with post-hoc testing using Fischer PLSD or Scheffe F-test.

Figure 3:
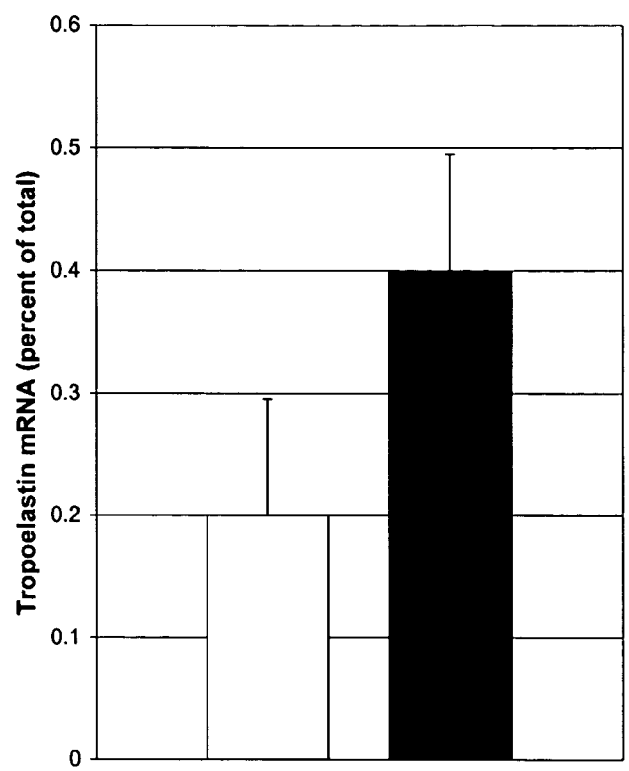
FIG. 3 is a graphical depiction of increase in tropoelastin content murine skin using a composition of the invention.

FIG. 2 shows specimens of the above, for comparison, with (A) being a specimen of the control (no additional zinc compound) and (B) of the invention. FIG. 3 depicts the increase in tropoelastin mRNA levels with treatment by the zinc-containing composition (black bar). This increase is paralleled by an increase in newly translated (hence soluble) tropoelastin by immunohistochemistry.

Example 7

Topical Application of a Zinc Formulation to Alter Epidermal Thickness, Elastin Content, and Hypodermal Fat

A stock zinc solution was prepared and applied as above in example 6. Paraffin-embedded specimens were sectioned at 4-6 microns, deparaffinized, and stained with Hematoxylin and Eosin stain. All procedures and analyses were done by blinded observers. Semi-quantitative scoring was done to measure cross-sectional epidermal thickness, elastin content, and hypodermal fat.

FIGS. 4, 5 and 6 show comparative scores for elastin content, epidermal thickness, and hypodermal fat, using semi-quantitative scales.

Example 8

Topical Application of a Zinc Formulation to Increase Skin Elasticity

Stock zinc solution was prepared as above to achieve a final concentration of 100 micromolar Zn++ in commercial moisturizer base. After addition to moisturizer bases, the samples were mixed homogeneity and stored at room temperature. Moisturizer was applied twice daily to the peri- and infra-orbital eye region. At baseline and each 7 day period later, video images were captured using Canon ZR60 (Canon, Jamesburg, N.J.). Snap time was determined as a measure of composite skin elasticity using Abode AfterEffects software.

FIGS. 7-11 show the results of tests on five human subjects treated for up to six weeks, as indicated.

Example 9

Effective Zinc Concentrations for Induction of Elastin Production

A stock zinc solution was prepared as above to achieve a final concentration of 100 micromolar Zn++ in commercial moisturizer bases. After addition to moisturizer bases, the samples were mixed homogeneity and stored at room temperature. At N=4 per group, C57 Black Six mice at 8 weeks of age were anesthesized with 3% isoflurance by inhalation. Moisturizer was applied daily to the dorsal skin of the mouse. Moisturizer was applied at 0.2 cc per day for each group for a 21-day period. After 21-day application, the treated dorsal skin was harvested and divided into three segments. One segment fixed in 10% neutral buffered formalin for 12-16 hours, then rinsed in 70% ethanol and embedded in paraffin. Two segments were frozen and stored.

Figure 12:
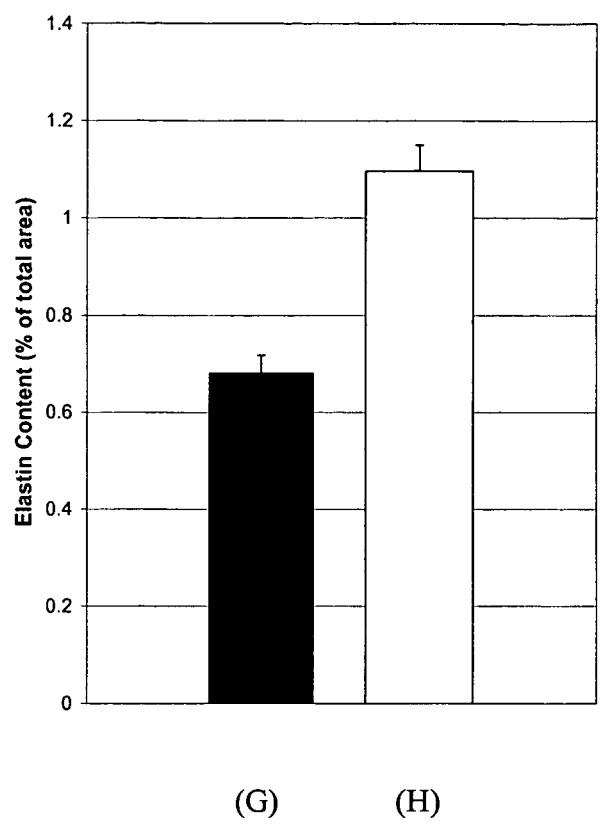
FIG. 12 is a graphical depiction of cross sectional elastin content after a 21-day topical application of zinc or control.

Paraffin-embedded specimens were sectioned at 4-6 microns, deparaffinized, and stained with verhoeff-van giesson elastica stain. All procedures and analyses were done by blinded observers. High resolution digital micrographs of each preparation we obtained using a Diagnostic Instruments SPOT camera (Diagnostic Instruments, Sterling Heights, Mich.) as displayed on a Nikon E600 epifluoresence microscope with a plan-apochromat lenses. Images were analyzed using Image Pro Discovery software (Media Cybernetics, Silver Spring, Md.) to determine total cross-sectional elastin content as % of total. Mean and standard error were assessed using Statview (Abacus Concepts, Berkeley, Calif.), with comparison made using ANOVA repeated measure and significance determined at 95% with post-hoc testing using Fischer PLSD or Scheffe F-test. Test results are shown in FIG. 12 (G—control; H—zinc-containing composition), which depicts cross-sectional elastin content after a 21-day topical application of zinc or control.

It also has been found that zinc, for example, zinc acetate, acts by stabilizing, then destabilizing, then restabilizing elastase function as the concentration of zinc-containing components increases. This pattern of activity likely contributes to floor and ceiling concentrations observed for induction of elastin production.

An assay was run that involved varying concentrations of each divalent cation, ranging from concentrations of 0.005M to 1.0M, in phosphate buffered saline (PBS). The positive control contained no cations, while the negative control contained no elastase. Solutions were read at 405 nm every minute for 15 minutes under controlled conditions. The optical density value of the negative control, which represented background interference, was subtracted from each result. These corrected optical density values from the two trials were averaged.

Elastase activity increased for all the ions $Mg^{2+}$, $Ca^{2+}$, and $Zn^{2+}$ between the interval of 0.005M to 0.01M cation concentration. At all cation concentrations greater than 0.01M, elastase activity sharply decreased, and higher concentrations continued to result in decreasing elastase activity toward a minimum value. Divalent cations were found to induce elastase activity at very low concentrations (<0.01M), followed by a range of concentrations where the presence of divalent cations inhibited elastase (0.01M~0.75M) to a minimum value greater than zero. At very high concentrations, divalent cations were found to once again induce elastase activity (>0.75M).

Figure 13:
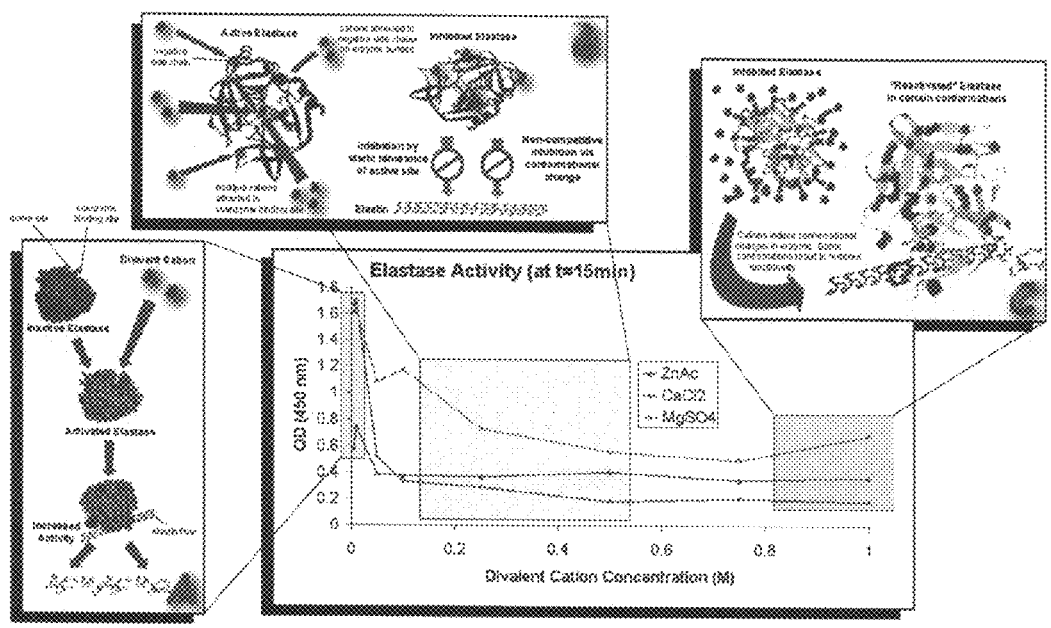
FIG. 13 contains graphical depictions of information from experiments conducted to investigate the effects of concentration on elastin production.

Elastase was found to be most sensitive to $Ca^{2+}$ ions (the most potent immediate inhibitor) while most constantly inhibited by $Zn^{2+}$ as time progressed. Elastase was least sensitive to $Mg^{2+}$. The results are shown in FIG. 13.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for increasing elastin content in a region of skin of a subject that is in need of increased elastin content, the method consisting essentially of applying topically a composition consisting essentially of one or more zinc-containing components in admixture with a dermatologically acceptable carrier to the region of skin of the subject, wherein the one or more zinc-containing components is selected from the group consisting of zinc acetate, zinc ascorbate, zinc aspartate, zinc butyrate, zinc caproate, zinc caprylate, zinc carbonate, zinc citraconate, zinc citramalate, zinc citrate, zinc EDTA, zinc formate, zinc fumarate, zinc gallate, zinc gluconate, zinc halides, zinc lactate, zinc malate, zinc maleate, zinc malonate, zinc metaphosphate, zinc monophosphate, zinc nitrate, zinc octoate, zinc orotate, zinc orthophosphate, zinc oxalate, zinc phosphate, zinc picolinate, zinc propionate, zinc pyrophosphate, zinc salicylate, zinc selenate, zinc succinate, zinc sulfate, zinc sulfonate, zinc tartrate, zinc tetrametaphosphate, zinc tripolyphosphate, zinc valerate, zinc amino acid complexes, zinc nucleotide complexes, and mixtures thereof, wherein zinc of the said one or more zinc-containing components is present in the composition at a concentration that increases elastin without causing epidermal sloughing and irritation due to zinc, wherein said concentration is in the range of 10 μM to 1.0 mM, and wherein the elastin content in the region of skin is increased.

2. The method according to claim 1, wherein the one or more zinc-containing components is zinc carbonate.

3. The method according to claim 1, wherein the one or more zinc-containing components is comprises zinc citrate.

4. The method according to claim 1, wherein zinc of the said one or more zinc-containing components is present in the composition at a concentration of 1.0 mM.

5. The method according to claim 2, wherein zinc of the said one or more zinc-containing components is present in the composition at a concentration of 1.0 mM.

6. The method according to claim 3, wherein zinc of the said one or more zinc-containing components is present in the composition at a concentration of 1.0 mM.

7. The method according to claim 1, wherein the region of skin is selected from the group consisting of the face, breasts, buttocks, neck, legs, arms, torso, and furrows or wrinkles in the face, hands or neck.

8. The method according to claim 1, wherein the carrier further comprises a moisturizer.

9. The method according to claim 1, wherein zinc of the said one or more zinc-containing components is present in the composition at a concentration of 10 μM.

10. The method according to claim 2, wherein zinc of the said one or more zinc-containing components is present in the composition at a concentration of 10 μM.

11. The method according to claim 3, wherein zinc of the said one or more zinc-containing components is present in the composition at a concentration of 10 μM.

* * * * *

```
SEQUENCE LISTING

<160> NUMBER OF SEQ ID NOS: 2

<210> SEQ ID NO 1
<211> LENGTH: 14
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<222> LOCATION: (1)..(1)
<223> OTHER INFORMATION: Guanine at position 1 is flourescein labeled

<400> SEQUENCE: 1
gcctggtgcc cact                                                       14

<210> SEQ ID NO 2
<211> LENGTH: 16
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<222> LOCATION: (1)..(1)
<223> OTHER INFORMATION: Cytosine at position 1 is flourescein labeled

<400> SEQUENCE: 2
ctccaccaag gccata                                                     16
```